United States Patent
Yang et al.

[11] Patent Number: 5,523,421
[45] Date of Patent: Jun. 4, 1996

[54] KOJIC ACID DERIVATIVES

[75] Inventors: Chang M. Yang, Seongnam; Jong Y. Hong; Ki W. Lee, both of Seoul; Byeong G. Lee, Suwon; Dong I. Chang, Anyang, all of Rep. of Korea

[73] Assignee: Pacific Corporation, Seoul, Rep. of Korea

[21] Appl. No.: 340,335

[22] Filed: Nov. 14, 1994

[30] Foreign Application Priority Data

Nov. 16, 1993 [KR] Rep. of Korea .................. 1993-24303

[51] Int. Cl.⁶ ................................................. C07D 309/40
[52] U.S. Cl. ............................................................ 549/418
[58] Field of Search ............................................ 549/418

[56] References Cited

FOREIGN PATENT DOCUMENTS

| | | |
|---|---|---|
| 54-92632A2 | 7/1979 | Japan . |
| 56-18569B2 | 4/1981 | Japan . |
| 56-77272A | 6/1981 | Japan . |
| 60-7961B2 | 2/1985 | Japan . |
| 60-9722B2 | 3/1985 | Japan . |
| 62-3820B2 | 1/1987 | Japan . |
| 64-83008A | 3/1989 | Japan . |
| 1-121205A | 5/1989 | Japan . |
| 2-28105A | 1/1990 | Japan . |
| 3-14508A | 1/1991 | Japan . |
| 4-145096A | 5/1992 | Japan . |
| 4-187618A | 7/1992 | Japan . |
| 5-39298A | 2/1993 | Japan . |

OTHER PUBLICATIONS

Nakagawa et al., Chem. Abstr., 116:59213p (1992) (Abstract of JP 03,223,275 (Oct. 2, 1991).

*Primary Examiner*—Nicky Chan
*Attorney, Agent, or Firm*—Nixon & Vanderhye

[57] ABSTRACT

Disclosed herein is novel kojic acid derivatives represented by the following formula (I):

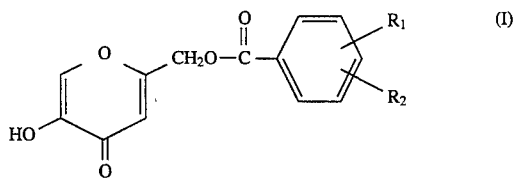

wherein, $R_1$ is a hydrogen atom or hydroxyl group; and $R_2$ is a hydroxyl group, having a strong activity of inhibiting tyrosinase, which is involved in a melanin formation.

The compounds of the present invention shows a stronger tyrosinase-inhibiting and radical scavenging activities, and has a low side effects to the human skin.

1 Claim, No Drawings

KOJIC ACID DERIVATIVES

BACKGROUND OF THE INVENTION

1. Field of the Invention

The present invention relates to novel kojic acid derivatives, and more particularly it relates to novel 2-mono- or di-hydroxybenzoic acid-substituted kojic acid derivatives having a strong skin whitening activity.

2. Description of Prior Art

Kojic acid, which is obtained from the culture of Aspergillus, has an activity of strongly inhibiting the action of tyrosinase, an enzyme involved in the formation of melanin, which is a major factor in determining the color of human skin. It has been reported that kojic acids inhibit the activity of tyrosinase by forming a chelate with the copper ion in the tyrosinase through the 5-hydroxyl and 4-carbonyl groups. Based on such tyrosinase-inhibiting activity of kojic acid, there have been proposed a lot of cosmetic compositions containing kojic acid as an active ingredient (See JP 56-18569B). Further, JP 54-92632A, JP 56-77272A, JP 60-7961B and JP 60-9722B disclose methods for improving the properties of kojic acid, such as storage stability, compatibility, solubility and the like, and various kojic acid derivatives such as kojic mono- or di-fatty acid esters, having an improved activity of inhibiting tyrosinase. Moreover, JP 3-14508A, JP-4-145096A, JP 4-187618A and JP 5-39298A propose various kojic acid derivatives having a strong tyrosinase-inhibiting activity, such as kojic ethers, glucosylated kojic acids and amino-protected amino acid kojic acids. Furthermore, JP 62-3820B, JP 64-83008A, JP 1-121205A and JP 2-028105A disclose compositions incorporating various additives in order to improve the solubility of kojic acid and to enhance the skin-whitening activity.

The present inventors made extensive researches to develop novel kojic acid derivatives having an improved tyrosinase-inhibiting activity as well as showing a decreased side effect to human skin. As a result thereof, we found that kojic acid derivatives of which the 2-hydroxymethyl group is substituted with mono- or di-hydroxybezoic acid show a superior inhibiting activity on tyrosinase. Particularly, 2-dihydroxybenzoyl kojic acid exhibits an excellent activity of scavenging the radicals, which are known to cause a skin aging, and a decreased side effect to skin.

SUMMARY OF THE INVENTION

Therefore, an object of the invention is to provide novel kojic acid derivatives having the following formula (I):

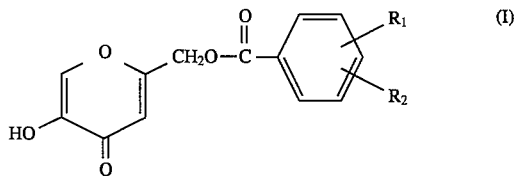

wherein, $R_1$ is a hydrogen atom or hydroxyl group; and $R_2$ is a hydroxyl group.

DETAILED DESCRIPTION OF THE INVENTION

The kojic acid derivatives (I) of the present invention may be prepared by the process shown in the following reaction scheme:

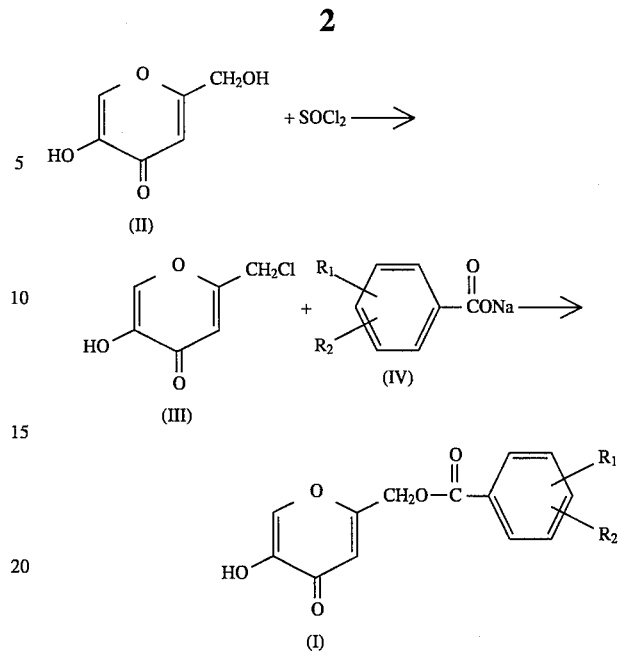

wherein, $R_1$ and $R_2$ and have the same meanings defined as above.

The compounds of the formula (IV) may include, for example sodium salts of 2-hydroxybenzoic acid, 3-hydroxybenzoic acid, 4-hydroxybenzoic acid, 2,3-dihydroxybenzoic acid, 2,4-dihydroxybenzoic acid, and of 3,4-dihydroxybenzoic acid.

The compounds of the formula (I) may include, but not limited thereto, 2-(2-hydroxybenzoyl)oxymethyl-5-hydroxy-4H-pyran-4-one, 2-(3-hydroxybenzoyl)oxymethyl-5-hydroxy-4H-pyran-4-one, 2-(4-hydroxybenzoyl)oxymethyl-5-hydroxy-4H-pyran-4-one, 2-(2,3-dihydroxybenzoyl)oxymethyl-5-hydroxy-4H-pyran-4-one, and 2-(3,4-dihydroxybenzoyl)oxymethyl-5-hydroxy-4H-pyran-4-one.

The novel kojic acid derivatives of the formula (I) according to the present invention may be prepared, as shown in the above reaction scheme, by reacting the kojic acid of the formula (II) with thionyl chloride($SOCl_2$) in a solvent such as chloroform to give 2-chloromethyl-5-hydroxy-4H-pyran-4-one("Chlorokojic acid") of the formula (III) and reacting the compound of the formula (IV) with the chlorokojic acid in a solvent such as N,N-dimethylformamide to give the present compound (I).

The compound of the formula (I) according to the present invention is of kojic acid derivative wherein the 2-hydroxymethyl group is substituted with hydroxybezoic acids and shows 5 to 20 folds higher activity than that of known kojic acid derivatives in terms of $IC_{50}$ (Concentration of kojic acid to inhibit the enzyme activity by 50%) (See Experimental Example 1 below). Particularly, the kojic acids substituted at the 2-position with dihydroxybenzoic acid, for example 2,3-dihydroxybenzoic acid, 2,4-dihydroxybenzoic acid or 3,4-dihydroxybenzoic acid, are capable of strongly inhibiting tyrosinase as well as can effectively scavenge the harmful radicals.

In general, radicals formed in the living body are known to cause a skin aging and a radical-scavenger can retard the skin aging(Japan Fragrance Journal, June, 1990, pp39–46). As scavengers of harmful radicals in the living body, vitamin E(tocopherol), hydroquinone, superoxide dismutase(SOD) and the like are known. The 2-dihydroxybenzoic acid substituted kojic acids (I) show a equivalent activity to that of those scavengers (See Experimental Example 2).

Further, it has been confirmed that the present compounds (I) has a little side effect to the human skin through a skin safety experiment (Experimental Example 3).

Accordingly, the present compounds (I) can be incorporated into cosmetic compositions or topical dermatic medicaments for the purposes of whitening the skin, preventing a tanning of skin or pigmentation.

The present invention will be illustrated hereinafter in more detail by way of non-limiting Examples. Examples 1 through 6 show the preparation and identification of the compounds (I); Experimental Example 1 compares the tyrosinase-inhibiting activity of the compounds (I) and of kojic acid; Experimental Example 2 compares the radicals-scavenging activity of the compounds (I) and of conventional anti-oxidants; and Experimental Example 3 shows a skin safety test of the compounds (I).

The method of preparing the intermediate compound (II) is illustrated in Reference Example.

REFERENCE EXAMPLE

Preparation of 2-chloromethyl-5-hydroxy-4H-pyran-4-one ("Chlorokojic acid")

50 g(351.8 mmol) of kojic acid was dissolved in 250 ml of N,N-dimethylformamide. The resulting solution was cooled in a ice bath of 10° C. and 30 ml(411.3 mmole) of thionyl chloride was added dropwise thereto. The mixture was stirred at a room temperature for 2 hours and 2000 ml of ice water was added. The precipitates were filtered and dissolved into 1000 ml of ethyl acetate. The reaction product was dried over magnesium sulfate, decolored with active charcoal and filtered. The filtrate was concentrated and hexane was added to give crystals, which was then dried under vacuum to give 37.5 g(66.83%) of the desired chlorokojic acid as a yellow solid.

mp.:165°–166° C.

TLC (in hexane:ethyl acetate=1:2) Rf=0.5

EXAMPLE 1

Preparation of 2-(4-hydroxybenzoyl)oxymethyl-5-hydroxy-4H-pyran-4-one 1.39 g(10.1 mmole) of 4-hydroxybenzoic acid and 0.4 g(10.1 mmole) of sodium hydroxide were dissolved into 40 ml of methanol. Residues obtained after distillating methanol was dissolved into 70 ml of N,N-dimethylformamide and 1.46 g(9.1 mmole) of chlorokojic acid prepared in Reference Example was added thereto. The resulting mixture was heated with stirring for 2 hours in an oil bath of 110° C. After distillating solvent, the residue was dissolved in 300 ml of ethyl acetate.

The ethyl acetate solution was washed with 5% chloric acid and distilled water, dried over magnesium sulfate, decolored with active charcoal and filtered. The filtrate was concentrated to give 1.64 g(68.7%) of 2-(4-hydroxybenzoyl) oxymethyl-5-hydroxy-4H-pyran-4-one as a solid.

mp.: 203°–205° C.(Decomposition)

TLC (in acetic acid: ethyl ether=25:1) Rf=0.62

$^1$N-NMR(DMSO-$d_6$, δ) 5.19(s, 2H), 6.51(s, 1H), 6.8–7.85(m, 4H) 8.08(s, 1H), 9.25(s, 1H), 10.27(s, 1H)

$^{13}$C-NMR(DMSO-$d_6$, δ) 61.90, 112.60, 121.13, 130.7, 135.76, 139.91, 146.01, 159.78, 161.20, 165.26, 173.59

EXAMPLE 2

Preparation of 2-(2-hydroxybenzoyl)oxymethyl-5-hydroxy-4H-pyran-4-one 1 g(6.2 mmole) of sodium salicylate and 0.9 g(15.6 mmole) of chlorokojic acid were dissolved into 70 ml of N,N-dimethylformamide. The resulting solution was heated with stirring for 2 hours in an oil bath of 110° C. After distillating solvent, the residue was dissolved in 300 ml of ethyl acetate. The ethyl acetate solution was washed with 5% chloric acid and distilled water, dried over magnesium sulfate, decolored with active charcoal and filtered. The filtrate was concentrated to give 0.85 g(58%) of 2-(2-hydroxybenzoyl) oxymethyl-5-hydroxy-4H-pyran-4-one as a solid.

mp.: 109°–200° C.

TLC (in ethyl ether:acetic acid=25:1) Rf=0.6

$^1$H-NMR(DMSO-$d_6$, δ) 5.22(s, 2H), 6.58(s, 1H), 6.9–7.8(m, 4H) 8.1(s, 1H), 9.26(s, 1H), 10.3(s, 1H)

$^{13}$C-NMR(DMSO-$d_6$, δ) 61.97, 112.64, 113.08, 117.5, 119.43, 130.4, 135.76, 139.95, 146.06, 159.71, 161.23, 167.26, 173.6

EXAMPLE 3

Preparation of 2-(3-hydroxybenzoyl)oxymethyl-5-hydroxy-4H-pyran-4-one

By following the procedure of Example 1 by employing 1.39 g(10.1 mmole) of 3-hydroxybenzoic acid, 0.4 g (10.1 mmole) of sodium hydroxide and 1.46 g(9.1 mmole) of chlorokojic acid, there was obtained 1.31 g(55.1%) of 2-(3-hydroxybenzoyl) oxymethyl-5-hydroxy-4H-pyran-4-one as a solid.

mp.:200°–201° C.

TLC (in ethyl ether:acetic acid =25:1) Rf=0.65

$^1$H-NMR(DMSO-$d_6$, δ) 5.20(s, 2H), 6.60(s, 1H), 7.1–7.65(m, 4H) 8.12(s, 1H), 9.09(s, 1H)

$^{13}$C-NMR(DMSO-$d_6$, δ) 61.92, 112.60, 116.2, 120.5, 121.81, 129.7, 131.15, 139.91, 146.01, 156.1, 161.20, 167.5, 173.59

EXAMPLE 4

Preparation of 2-(3,4-dihydroxybenzoyl)oxymethyl-5-hydroxy-4H-pyran-4-one

By following the procedure of Example 1 by employing 4.22 g(27.4 mmole) of 3,4-dihydroxybenzoic acid, 1.1 g (27.5 mmole) of sodium hydroxide and 4 g(24.9 mmole) of chlorokojic acid, there was obtained 3.0 g(43.3%) of 2-(3, 4-dihydroxybenzoyl)oxymethyl-5-hydroxy-4H-pyran-4-one as as a solid.

mp.:226°–228° C.(Decomposition)

TLC (in hexane:ethyl ether=1:2) Rf=0.27

$^1$H-NMR(DMSO-$d_6$, δ) 5.12(s, 2H), 6.49(s, 1H), 6.8–7.38(m, 3H) 8.1(s, 1H), 9.24(br, 1H), 9.44(br, 1H), 9.88(br, 1H)

$^{13}$C-NMR(DMSO-$d_6$, δ) 61.95, 112.60, 115.13, 116.54, 121.03, 122.18, 139.91, 144.79, 146.01, 150.14, 161.20, 166.5, 173.59

EXAMPLE 5

Preparation of 2-(2,3-dihydroxybenzoyl)oxymethyl-5-hydroxy-4H-pyran-4-one

By following the procedure of Example 1 by employing 1.0 g(6.5 mmole) of 2,3-dihydroxybenzoic acid, 0.26 g (8.5 mmole) of sodium hydroxide and 0.92 g(7.6 mmole) of chlorokojic acid, there was obtained 0.8 g(50.2%) of 2-(2, 3-dihydroxybenzoyl)oxymethyl-5-hydroxy-4H-pyran-4-one as a solid.

m.p.:199°–201° C.

TLC (in hexane: ethyl acetate=1:2) Rf=0.35

¹H-NMR(DMSO-d₆, δ) 5.17(s, 2H), 6.54(s, 1H), 6.68–7.27(m, 3H) 8.12(s, 1H), 9.25(br, 2H)

¹³C-NMR(DMSO-d₆, δ) 61.97, 112.60, 113.04, 118.2, 120.17, 120.33, 139.96, 145.5, 146.06, 150.86, 161.23, 167.26, 173.61

EXAMPLE 6

Preparation of 2-(2,4-dihydroxybenzoyl)oxymethyl-5-hydroxy-4H-pyran-4-one

By following the procedure of Example 1 by employing 4.22 g(27.4 mmole) of 2,4-dihydroxybenzoic acid, 1.1 g (27.5 mmole) of sodium hydroxide and 4 g(24.9 mmole) of chlorokojic acid, there was obtained 5.7 g(85.3%) of 2-(3, 4-dihydroxybenzoyl)oxymethyl-5-hydroxy-4H-pyran-4-one as a solid.

mp.:213°–215° C.(Decomposition)

TLC (in hexane:ethyl acetate=1:2) Rf=0.4

¹H-NMR(DMSO-d₆, δ) 5.24(s, 2H), 6.60s, 1H), 6.32–7.68(m, 3H) 8.13(s, 1H), 9.33(br, 1H), 9.8(br, 2H)

¹³C-NMR(DMSO-d₆, δ) 62.02, 102.12, 4.24, 107.96, 112.65 131.91, 139.97, 146.15, 159.78, 159.78 161.26, 162.25, 167.26, 173.63

In order to examine the tyrosinase-inhibiting activity, harmful radicals-scavenging activity and the skin safety of the present kojic acid derivatives, the following test were carried out by employing the compounds of Examples 1 through 6.

EXPERIMENTAL EXAMPLE 1

Tyrosinase-inhibiting activity

Tyrosinase-inhibiting activity of the compounds of Examples 1 through 6 were compared with that of kojic acid as follows:

<Method>

As an enzyme, the tyrosinase, which was extracted from mushroom and produced by SIGMA was purchased. Tyrosine, a substrate was dissolved into distilled water to a concentration of 0.3 mg/ml and each 1.0 ml of the solution was placed into a test tube. 1.0 ml of potassium sulfate buffer(0.1M, ph 6.8), 0.9 ml of stepwise dilutions of compounds of Examples 1 through 6 or kojic acid were added thereto. The resulting mixture was reacted in a 37° C. incubator for 10 minutes. Ethanol and water were used to dilute the test compounds. As a control, 0.9 ml of 1:1 mixture of ethanol and water was used.

0.1 ml of tyrosine solution (2,500 unit/ml) was added and the reaction mixture was reacted in a 37° C. incubator for 10 minutes. The test tube was quickly cooled in an ice water bath to stop the reaction, and the absorbance was measured at 475 nm. The tyrosinase-inhibiting activities of the compounds of Examples 1 through 6 and kojic acid were calculated by employing the following equation:

$$\text{Inhibition of tyrosinase (\%)} = 100 - \frac{\text{Absorbance of test compound}}{\text{Absorbance of control}} \times 100$$

From the inhibitions(%) of tyrosinase by a series of dilutions of test compounds, IC₅₀, i.e., a concentration of test compound which inhibit the tyrosinase by 50% was calculated for each test compound.

<Results>

The results are shown in Table 1.

TABLE 1

| Test Compounds | IC₅₀ (μM) |
| --- | --- |
| Kojic acid | 80 |
| Compound in Example 1 | 10 |
| Compound in Example 2 | 15 |
| Compound in Example 3 | 15 |
| Compound in Example 4 | 4 |
| Compound in Example 5 | 14 |
| Compound in Example 6 | 6 |

As can be seen from the results in Table 1, the compounds of Example 1 through 6 show 5 to 20 folds higher activity of inhibiting tyrosinase than that of kojic acid, and particularly the compounds of Examples 4 and 6 exhibit the strongest tyrosinase-inhibiting activity.

EXPERIMENTAL EXAMPLE 2

Radicals-scavenging activity

Harmful radicals-scavenging activity of the compounds of Examples 1 through 6 were compared with those of conventional anti-oxidants by using DPPH(diphenylpicrylhydrazyl) radical-scavenging test as follows:

<Method>

DPPH was dissolved into ethanol to a concentration of 100 μM. A series of dilutions of compounds of Examples 1 through 6, vitamin C, vitamin E or hydroquinone were prepared.

Ethanol and water were used to dilute the test compounds. As a control, 1:1 mixture of ethanol and water was used. The series of dilutions of each test compound were mixed with 1,900 μl of DPPH solution and the dilution solvent was added to 2.0 ml. The resulting mixture was reacted in a 37° C. incubator for 30 minutes. The absorbance was measured at 515 nm. The radical-scavenging activities of the compounds of Examples 1 through 6 and conventional anti-oxidants were calculated by employing the following equation:

$$\text{Radical scavenging activity (\%)} = 100 - \frac{\text{Absorbance of test compound}}{\text{Absorbance of control}} \times 100$$

From the radical scavenging activity(%) by a series of dilutions of test compounds, IC₅₀, i.e., a concentration of test compound which scavenge the radical, DPPH by 50% was calculated for each test compound.

<Results>

The results are shown in Table 2.

TABLE 2

| Test Compounds | IC₅₀ |
| --- | --- |
| Compound in Example 1 | 1.91 mM |
| Compound in Example 2 | 2.23 mM |
| Compound in Example 3 | 2.03 mM |
| Compound in Example 4 | 11.5 μM |
| Compound in Example 5 | 11.3 μM |
| Compound in Example 6 | 15.0 μM |
| Vitamin C | 29.2 μM |
| Vitamin E | 34.8 μM |
| Hydroquinone | 25.4 μM |

As can be seen from the results in Table 2, the compounds of Examples 4 through 6, i.e., 2-dihydroxybenzoyl-substituted kojic acid show a strong activity of scavenging radical.

EXPERIMENTAL EXAMPLE 3

Safety in the living body

In order to examine the safety of the compounds of Examples 1 through 6, the human body patch test was carried out as follows:

<Method>

The brachium of thirty(30) healthy volunteers (15 females and 15 males) was thoroughly washed with 70% ethanol and applied with a finn chamber containing 20 μl of a conventional creamy preparation incorporating 0.2 wt % of one of the compound of Examples 1 to 6. The finn chamber was thoroughly bonded to the brachium using an adhesive tape. 48 hours later, the tape and chamber were removed, and the adherent site of the arm was wiped with a gauze to remove the remaining preparation and observed for redness(erythma), swelling, and papuol. 48 hours later, the site was examined again.

<Results>

The results are shown in Table 3.

TABLE 3

| Test Preparations | 48 hours later | 96 hours later |
|---|---|---|
| Control | 0/30 | 0/30 |
| Containing Compd in Ex. 1 | 0/30 | 0/30 |
| Containing Compd in Ex. 2 | 2/30 | 0/30 |
| Containing Compd in Ex. 3 | 1/30 | 1/30 |
| Containing Compd in Ex. 4 | 1/30 | 0/30 |
| Containing Compd in Ex. 5 | 1/30 | 0/30 |
| Containing Compd in Ex. 6 | 0/30 | 0/30 |

The results are shown in terms of the number of positive subject/the number of total subjects.

As can be seen from the results in Table 3, although the preparations containing the compounds of Examples 2 through 5 show a weak positive response after 48 hours, these responses except that containing the compound of Example 3 are disappeared after 96 hours. Accordingly, the compounds of Examples 1, 2, 4, 5 and 6 are safe to the human skin and the compound of Example 3 is considered to be safe because only one(1) among 30 subjects show a weak positive response.

What is claimed is:

1. A kojic acid derivative represented by the formula (I):

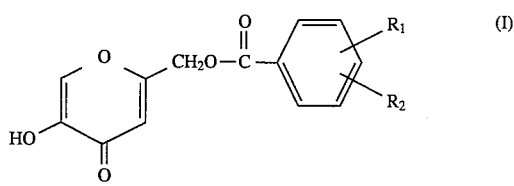

wherein $R_1$ is a hydroxyl group; and $R_2$ is a hydroxyl group.

* * * * *